United States Patent
Barua et al.

(10) Patent No.: US 10,329,528 B2
(45) Date of Patent: Jun. 25, 2019

(54) METHOD OF FORMING MICROPARTICLES FOR USE IN CELL SEEDING

(71) Applicants: Sutapa Barua, Rolla, MO (US); Chase Herman, Nixa, MO (US)

(72) Inventors: Sutapa Barua, Rolla, MO (US); Chase Herman, Nixa, MO (US)

(73) Assignee: The Curators of the University of Missouri, Columbia, MO (US)

( * ) Notice: Subject to any disclaimer, the term of this patent is extended or adjusted under 35 U.S.C. 154(b) by 5 days.

(21) Appl. No.: 15/480,805

(22) Filed: Apr. 6, 2017

(65) Prior Publication Data

US 2017/0292109 A1   Oct. 12, 2017

Related U.S. Application Data (60) Provisional application No. 62/318,837, filed on Apr. 6, 2016.

(51) Int. Cl.
| | | |
|---|---|---|
| *C12N 5/00* | (2006.01) | |
| *C08L 67/04* | (2006.01) | |
| *B29B 9/12* | (2006.01) | |
| *C08G 63/08* | (2006.01) | |

(52) U.S. Cl.
CPC .............. *C12N 5/0075* (2013.01); *B29B 9/12* (2013.01); *C08G 63/08* (2013.01); *C08L 67/04* (2013.01); *B29B 2009/125* (2013.01); *C12N 2533/40* (2013.01); *C12N 2533/52* (2013.01); *C12N 2533/54* (2013.01); *C12N 2537/00* (2013.01)

(58) Field of Classification Search
CPC ........... C08G 63/08; C08L 67/04; B29B 9/12; B29B 2009/125; C12N 2533/40
See application file for complete search history.

(56) References Cited

U.S. PATENT DOCUMENTS

| 8,530,415 B2 | 9/2013 | Naughton et al. | |
| 2005/0037086 A1* | 2/2005 | Tyo | A61K 9/1694 424/489 |
| 2005/0107876 A1 | 5/2005 | Kim et al. | |
| 2010/0069602 A1* | 3/2010 | Raiche | A61K 9/1647 528/354 |

OTHER PUBLICATIONS

McCall, R.L., et al.; Journal of Visualized Experiments, Dec. 2013, p. 1-8.*
He, Yunfan, et al, article, "Development of Synthetic and Natural Materials for Tissue Engineering Applications Using Adipose Stem Cells", Hindawi Publishing Corporation, *Stem Cells International*, vol. 2016, Article ID 6786247 (12 pgs).
Newman, Kimberley D., et al., Article, "Poly(D,L lactic-co-gycoloic acid) Microspheres as Biodegradable Microcarriers for Pluripotent Stem Cells", *Biomaterials* 25 (2004) pp. 5763-5771 (9 pgs).
Seo, Seogjin et al., Article, "Mesenchymal stem Cell-Based Tissue Engineering for Chondrogenesis", Hindawi Publishing Corporation, *Journal of Biomedicine and Biotechnology*, vol. 2011, Article ID 806891 (8 pgs).
Balmert, Stephen C. et al., NIH-PA Author Manuscript, "Biomimetic Delivery with Micro- and Nanoparticles", Adv Mater: Jul. 24, 2012; 24(28): 3757-3778 (40 pgs).
Lee, Young Sook et al., "Development of Porous PLGA/PEI 1.8k Biodegradable Microspheres for the Delivery of Mescenchymal Stem Cells (MSCs)", *Journal of Controlled Release*, vol. 205 (2015) pp. 128-133 (6 pgs).

* cited by examiner

*Primary Examiner* — Robert S Jones
(74) *Attorney, Agent, or Firm* — Stinson Leonard Street LLP

(57) ABSTRACT

The present invention is directed to methods for forming microparticles useful for cell seeding and for conjugating protein to the surface of the microparticles. The method comprises co-injecting an organic solution of PLGA or other polymer with an aqueous solution into a flow focusing tube.

65 Claims, 9 Drawing Sheets

METHOD OF FORMING MICROPARTICLES FOR USE IN CELL SEEDING

CROSS-REFERENCE TO RELATED APPLICATIONS

This application is based on and claims priority to U.S. Provisional Application Ser. No. 62/318,837, filed on Apr. 6, 2016, which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention is directed to the field of microparticle formation for use in growing cells.

2. Description of Related Art

Cell therapy is an emerging strategy to replace or repair severely damaged tissues with cultured cells. However, structural supports are required for cells to form the tissue. Biodegradable porous polymeric microparticles have been studying as scaffolds for cell growth.

BRIEF SUMMARY OF THE INVENTION

One aspect of the present invention is directed to a method for forming microparticles useful for cell seeding. In one such aspect, the method includes obtaining an organic solution comprising poly(D,L-lactide-co-glycolide) (PLGA), obtaining a first aqueous solution comprising polyvinyl alcohol (PVA) and obtaining a second aqueous solution comprising PVA in a higher concentration than said first aqueous solution. The organic solution and a carrier stream of the first aqueous solution are injected into a flow focusing tube to form organic droplets within the carrier stream. The carrier stream comprising the organic droplets is introduced into the second aqueous solution to form microparticles of the PLGA in the second aqueous solution. The organic solvent is evaporated and the PVA is removed.

In some aspects of the invention, the ratio of the PLGA to the organic solvent is from 1% (w/v) to 25% (w/v), or from 5% (w/v) to 15% (w/v). In some aspects of the invention, the organic solution comprises PLGA and polyethylene glycol (PEG). In some such aspects, the ratio of PLGA to PEG is 70:1 or greater.

In some aspects of the invention the concentration of PVA in the first aqueous solution is from 1% (w/v) to 10% (w/v), and the concentration of PVA in the second aqueous solution is from 1% (w/v) to 10% (w/v). In other aspects of the invention, the ratio of the organic solution to the first aqueous solution is 1:1 to 1:10, or 1:2 to 1:4. In yet other aspects of the invention, the ratio of the organic solution to the first aqueous solution to the second aqueous solution is from 1:1:5 to 1:5:25.

In some aspects of the invention, the introducing step comprises submerging an outflow end of the flow focusing tube in the second aqueous solution. In other aspects of the invention, the introducing step comprises stirring the second aqueous solution, which may be conducted at a speed from 100 to 300 rpm. In yet other aspects of the invention, the second aqueous solution is further stirred after the introducing step.

In some aspects of the invention, the PLGA microparticles are lyophilized. In other aspects of the invention, the PLGA microparticles are stretched into microdisks and microrods.

Other aspects of the invention are directed to a method of conjugating a cell binding protein to surfaces of poly(D,L-lactide-co-glycolide) (PLGA) microparticles. In some such aspects of the invention, the PLGA microparticles comprise PLGA-PEG microparticles. In some aspects of the invention, the process includes obtaining PLGA microparticles formed from the process of claim 1. The PLGA microparticles are suspended in an aqueous buffer solution at pH from 5.5 to 6.5. The carboxyl groups on the surfaces of the PLGA microparticles are activated, and protein is added at a pH above 7.0. The protein and PLGA microparticles are shaken to conjugate the protein to the surfaces of the PLGA microparticles, and unreacted reagents are removed. In some aspects of the invention, the shaking step is combined with or followed by deaggregating the mixture. In other aspects of the invention, the unreacted reagents are removed by centrifugation, filtration or combinations thereof.

In some aspects of the invention, the ratio of the PLGA microparticles to the buffer solution is 1:1 to 25:1 (w/v). In other aspects of the invention, the protein is selected from the group consisting of fibronectin, gelatin, collagen, laminin and peptides.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to methods of forming microparticles useful for cell seeding and for conjugating protein to the surface of the microparticles.

One aspect of the invention is directed to methods of forming microparticles using a flow focusing device. The method comprises obtaining an organic solution comprising a biodegradable and biocompatible polymer, such as poly (D,L-lactide-co-glycolide) (PLGA). Two aqueous solutions comprising a surfactant, such as polyvinyl alcohol (PVA), are also obtained. The organic solution is co-injected with a stream of the first aqueous solution, referred to herein as a "carrier" stream, into a flow focusing tube. The combined streams are introduced into the second aqueous solution to form microparticles of the PLGA in the second aqueous solution. The organic solvent is then evaporated and the PVA removed.

The biodegradable and biocompatible polymer is preferably PLGA. However, other polymers, for example polycaprolactone (PCL) in dichloromethane (DCM), can also be used. Also, PLGA may be combined with polyethylene glycol (PEG) or other polymers. The PEG is preferably physically adsorbed to PLGA microparticles. Although PLGA will be referred to in the following description, it should be understood that the description also applies to other polymers and polymer combinations.

The organic solvent can generally be any organic solvent. Exemplary organic solvents include halogenated hydrocarbons (e.g. chloroform and dichloromethane), ethyl acetate, acetone, dioxin and tetrahydrofuran. In some embodiments, ethyl acetate is used. The ratio of PLGA to solvent is preferably 1% to 25% (w/v) (e.g. 10 mg/ml to 250 mg/ml), more preferably 5% to 15%, and most preferably 7% to 12%. In some embodiments, the PLGA is present at 200 mg/ml, or approximately 10% (w/v). When a second polymer such as PEG is present, the ratio of PLGA to PEG is preferably greater than 70:1 (w/w), more preferably greater than 80:1 (w/w) and most preferably around 90:1 (w/w).

The aqueous solutions comprise a surfactant. PVA is a commonly used surfactant that has been shown to be useful in the present invention, although other surfactants can also be used. Although PVA will be referred to in the following description, it should be understood that the description also applies to such other surfactants.

The aqueous solutions can generally comprise any aqueous solvent. Water can be used consistent with the present invention, and use of reverse osmosis (RO) water prevents any external debris during microparticle synthesis. Two aqueous solutions are provided. The first aqueous solution acts as a carrier stream when co-injected with a stream of the organic solution. When the organic solution and first aqueous solution are co-injected, the organic solution forms organic droplets within the carrier stream. More specifically, when a fixed amount of the organic solution is mixed with a larger volume of the first aqueous solution, emulsification will spontaneously occur, thus creating spherical droplets of the organic solution. The organic solvent will then slightly diffuse into the first aqueous solution. The mixture is introduced into the second aqueous solution, having a higher concentration of PVA, which acts a hardening bath to maintain the size of the microparticles. If left open to the atmosphere, the organic solvent will evaporate out of the mixture, leaving behind spherical polymer particles. Several variables can be modulated to control the size of these particles. These variables include: method of combining the organic and aqueous phases, intensity of mechanical agitation upon addition, length of agitation time, length of evaporation time, organic solvent, polymer species, polymer concentration, emulsifier additives in the aqueous phase, concentrations of emulsifiers, relative amounts of the two phases, ambient conditions, and other variables that will be understood by those of ordinary skill in the art.

The concentration of PVA in both the first and second aqueous solutions is preferably from 1% to 10% (w/v). The concentration of PVA in the second aqueous solution may be higher than the concentration of PVA in the first aqueous solution Lower PVA concentrations make larger microparticles, whereas higher PVA concentrations from smaller microparticles. The concentration of PVA in the first aqueous solution is preferably less than 5%, preferably, less than 3%, more preferably around 1% (w/v) and the concentration of PVA in the second aqueous solution is preferably greater than 5%, preferably greater than 8%, more preferably around 10% (w/v). The first and second aqueous solutions may comprise the same surfactant and same aqueous solvent.

The organic solution and first aqueous "carrier" solution are co-injected into a flow focusing device using any suitable method, as will be understood by one of ordinary skill in the art. A stream of the organic solution and a carrier stream of the first aqueous solution may be co-injected using a pump(s), such as a two-syringe pump, in which the two syringes are filled with the organic solution and first aqueous solution, respectively. The pump can maintain the flow rate of the solutions, which assists with homogeneous production of microparticles.

Co-injecting the organic solution and carrier aqueous solution results in the formation of organic droplets in the carrier aqueous solution, as described above. The ratio of the organic solution to the first aqueous solution is preferably 1:1 to 1:10, more preferably is 1:2 to 1:4 (v/v). In some embodiments, the ratio of the organic solution to the first aqueous solution is 3:10 (v/v).

The flow focusing tube into which the stream of organic solution and carrier stream of carrier aqueous solution are co-injected can be any tube suitable for such purpose. In some embodiments, the tube is from 9 to 12 inches in length and 0.1 to 0.4 inches, preferably 0.2 to 0.3 inches, in diameter. A Pasteur pipette, such as a 9 inch Pasteur pipette, can be used consistent with the invention.

The carrier stream comprising the organic droplets can be introduced into the second aqueous solution by any suitable method, as will be readily understood by one of ordinary skill in the art. In some embodiments, the outflow end of the flow focusing tube is submerged in the second aqueous solution. The second aqueous solution may be stirred during the introducing process. The second aqueous solution may be stirred at 100 to 300 rpm, and in some embodiments is stirred at around 250 rpm. The time for which the introducing step is carried out can vary depending on the v/v ratio and flow rates. In some embodiments, the introducing step is carried out for three minutes. The ratio of organic solution to the first aqueous solution to the second aqueous solution is preferably from 1:1:5 to 1:5:25 (v/v/v). In some embodiments the ratio is 3:10:75 (v/v/v).

When the carrier stream comprising the organic droplets is introduced into the second aqueous solution, microparticles of the PLGA are formed in the second aqueous solution. The microparticles are generally spherical in shape. The method of the present invention can produce PLGA microparticles with varying sizes, including sizes ranging from 100-300 μm, including 150-250 μm.

After the carrier stream is introduced into the second aqueous solution, the solution can be further stirred for a period of time. For example, the second aqueous solution can be stirred for 15 to 60 minutes after the carrier stream is introduced.

The organic solvent is then evaporated. The solvent may be evaporated at room temperature. In such embodiments, the evaporation is preferably carried out for 18 or more hours.

The process also preferably includes removing the PLA. In some embodiments, the PLA is removed by centrifugation, which may be followed by water washes. The remaining PLGA microparticles may then be lyophilized.

In certain applications it is desirable to produce PLGA microparticles with different shapes. Non-spherical PLGA microparticles can be produced by stretching the PLGA microparticles into microdisks and microrods. Stretching can be carried out according to the methods described in Ho, C. C., et al.: Preparation of monodisperse ellipsoidal polystyrene particles. *Colloid and Polymer Science*, 271, 469-479; Champion, J. A.; Mitragotri, S.: Role of target geometry in phagocytosis. *Proceedings of the National Academy of Sciences of the United States of America* 2006, 103, 4930-4934; and Barua, S., et al.: Particle shape enhances specificity of antibody-displaying nanoparticles. *Proceedings of the National Academy of Sciences of the United States of America* 2013, 110, 3270-3275 which are incorporated herein for purposes of such disclosure.

A second aspect of the invention is directed to a method of conjugating a cell binding protein to surfaces of microparticles. The process can be used with the microparticles formed by the process of the present invention, or with biodegradable soft polymeric microparticles formed by other processes. Although PLGA microparticles will be referred to in the following description, it should be understood that the description also applies to other microparticles.

Microparticles, such as the PLGA microparticles formed from the process described above, are suspended in an aqueous buffer solution. The buffer solution preferably has a pH from 5.5 to 6.5, preferably 5.7 to 6.3 and in some embodiments, around 6.0. The ratio of the PLGA microparticles to the buffer solution can be 1:1 to 25:1 (w/v), 5:1 to 15:1, and in some embodiments around 10:1 (w/v). Any suitable buffer may be used, as will be readily understood by one of ordinary skill in the art. A buffer comprising (morpholino)ethanesulfonic acid (MES) and NaCl is suitable for use with the invention. In some embodiments, 50 mg of PLGA microparticles may be suspended in 5 ml of an aqueous activation buffer comprising 0.1 M 2-mES and 0.5 M NaCl with an adjusted pH of 6.0.

The carboxyl groups on the surfaces of the PLGA microparticles are then activated. The activation may include addition of synthetic groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters, or other suitable groups, as will be readily understood by one of ordinary skill in the art. In some embodiments, the carboxyl groups are activated by successive additions of 1-Ethyl-3-(3-dimethylaminopropyl)carbodiimide (EDC) and N-hydroxysuccinimide (NHS) to produce an amine-reactive NHS ester on the surfaces of the PLGA microparticles. For example, activation of carboxyl groups on the PLGA microparticle surface can be accomplished through the successive additions of 4 mg of EDC and 6 mg of NHS to yield an amine-reactive NHS ester.

The protein is then added to form a mixture of the microparticles and the protein. Prior to addition of the protein the pH is adjusted, preferably to above 7.0, more preferably to above 7.2 and in some embodiments to around 7.4. Prior to adding the protein, a portion of the buffer comprising a mass of the microparticles in the desired amount may be removed from the buffer solution for protein addition. The protein may be any cell binding protein, as will be recognized by one of ordinary skill in the art. Suitable proteins include fibronectin, gelatin, collagen, laminin and peptides. In some embodiments, the ratio of protein to microparticles can be 0.01:1 to 1:1, and in some embodiments is around 0.05:1 (w/w). Fibronectin is a natural glycoprotein originating on the extracellular matrix of embryonic and adult tissues that binds to the $\alpha_5\beta_1$ receptor on cell surface. Fibronectin aids in cell adhesion through specific receptor ligand interactions. It helps wound healing with the help of adherent fibroblast cells, fibrin cross-linker and collagen fibrils.

The mixture is then shaken to conjugate the protein to the surfaces of PLGA microparticles. At lower temperatures, longer incubation times are required. For example, at 4° C., the shaking may be carried out for 10 hours, whereas at 25° C., the reaction time could be reduced down to 2 hours. The shaking may be carried out at around 450 rpm. The mixture may be deaggregated, for example by using polyethylene glycol (PEG) to the mixture. PEG may be added to a final concentration of 0.001% PEG.

Unreacted reagents may then be removed. Removal of unreacted reagents can be accomplished using centrifugation, filtration or combinations thereof, and may be accompanied by water washes to achieve pure, protein-conjugated microparticles.

The present invention provides a new method of polymer microparticle synthesis, and non-spherical microparticle formation for growing cells on the surface of microparticles. The present invention enables synthesis of PLGA microparticles of a desired size (e.g. 150-200 µm) using a single emulsion solvent evaporation method which utilizes a flow-focusing device. Using the flow-focusing devices facilitates production of particles of desired size, in a short amount of time. It has been found 150 mg of microparticles in the 150-200 µm range can be produced in under two hours, whereas other existing methods have had trouble reaching this size of particle and have required over 24 hours for production. The process of the invention can be scaled up tenfold to produce 1.5 g of particles by increasing the poly(vinyl alcohol) (PVA) hardening bath to 1 L, and the time required would not increase. The microparticle synthesis method of the invention does not require a custom-built apparatus or chemically complex solutions (e.g. salt/protein solutions for stabilization of double emulsions, or room temperature ionic liquids). Additionally, multiple syntheses could be conducted in tandem to increase production dramatically, while still minimizing personnel. Particles are currently produced at a rate of 2000 particles per dollar.

The method of the present invention prepares layer-by-layer microparticles with a PLGA core, and fibronectin (or other protein) and/or polyethylene glycol polymer on the surface of the PLGA, using one-step single emulsion. Conventional batch emulsification requires at least two steps in which internal droplets of particles are formed in surfactant 1 at step 1 for at least 24 h followed by outer droplet formation by shear at step 2 with an additional 24 h. In the method of the present invention, both surfactant and particle mixtures are added at the same time in less than an hour. The parallel streams of particles and surfactants are focused through a constriction that breaks up into droplets through the gap.

The present invention can produce particle geometries that are important for eliciting cell alignment to dictate tissue microarchitectures and biological functions. The aligned organization of cells is important to regulate cell-matrix organization. As described in Example 3, below, the PLGA microparticles with three different topographical geometries where shown to proliferate in an in vitro bioreactor that provides an effective approach to provide appropriate cushioning for cell survival. While there has been an interest in growing cells on various shapes of microparticles, synthesis of monodisperse spherical PLGA microparticles and non-spherical shape PLGA particles has been a challenge. The invention includes a new technique that can be used in spherical and non-spherical microparticle synthesis.

Certain aspects of the invention are illustrated by the following non-limiting examples.

Example 1: Microparticle Formation

Synthesis of PLGA Microparticles

Firstly, an organic solution was formulated by dissolving 200 mg of Poly(D,L-lactide-co-glycolide) (PLGA; Acros Organics, ~19 kDa) in 3 ml of ethyl acetate (Fisher Scientific). Aqueous solutions of 1% and 10% (w/v) polyvinyl alcohol (PVA; Sigma-Aldrich, 30-70 kDa) were formed by dissolving PVA in reverse osmosis (RO) water. A flow-focusing apparatus was assembled with 3 and 10 ml syringes, a two-syringe pump (kdScientific, KDS-200), plastic tubing, a Pasteur pipette, and a stir plate. The 3 and 10 ml syringes were completely filled with the PLGA and 1% PVA solutions, respectively; these represent the organic and the aqueous carrier streams of the flow-focusing apparatus.

By using an equal drive block velocity on both syringes, the two streams were injected into the Pasteur pipette at a 3:10 flow rate differential. With careful adjustments, gently forcing the organic stream tubing into the pipette neck produced regularly-sized organic droplets surrounded by the aqueous carrier stream in the pipette capillary. The Pasteur pipette was positioned vertically above 75 ml of the 10% PVA solution (stirring at approximately 250 rpm) such that the pipette tip was just submerged near the center of the solution's vortex whorl. For 3 minutes of injection, the organic droplets were dispersed into the continuous aqueous phase. The Pasteur pipette was then removed, and the emulsion was stirred for an additional 15 minutes. The mixture was left undisturbed overnight (>18 hours) to allow for evaporation of residual ethyl acetate at room temperature. PVA was removed by centrifugation at 7,000 rcf, followed by five washes with RO water. Microspheres were then lyophilized, weighed, and stored at 4° C. PLGA microspheres were stretched to microdisks and microrods by the film stretching technology.

Synthesis of PLGA-PEG Microparticles

PLGA-PEG microparticles were prepared using a modified version of the single emulsion-solvent evaporation technique, utilizing a flow-focusing apparatus as described above. PLGA particles with physically adsorbed PEG were prepared in the same manner but at a PLGA:PEG (w/w) ratio of 90:10, thus 180 mg of PLGA and 20 mg of PEG were used. An aqueous solution comprising of 1% (w/v) polyvinyl alcohol (PVA; Sigma-Aldrich, 30-70 kDa, 87-90% hydrolyzed) was formed by dissolving PVA in reverse osmosis (RO) water.

Example 2: Protein (Fibronectin or Gelatin) Conjugation to the Surface of PLGA and PLGA-PEG Microparticles Bovine fibronectin (R&D Systems) and gelatin were conjugated to the surface of PLGA microparticles, including PLGA-PEG microparticles, by coupling primary amines of fibronectin with carboxyl groups of PLGA to form amide bonds (NHS and Sulfo-NHS Instructions, Thermo Scientific). Briefly, 50 mg of microparticles were suspended in 5 ml of an aqueous activation buffer: 0.1 M 2-(morpholino) ethanesulfonic acid (MES; Sigma-Aldrich) and 0.5 M NaCl (Fisher Scientific) with an adjusted pH of 6.0. Activation of carboxyl groups on the PLGA microparticle surface was accomplished through the successive additions of 4 mg of 1-Ethyl-3-(3-dimethylaminopropyl)carbodiimide (EDC; Thermo Scientific) and 6 mg of N-hydroxysuccinimide (NHS; Thermo Scientific) to yield an amine-reactive NHS ester. After increasing the mixture pH above 7.0, a volume containing the desired particle mass for cell seeding was removed, and fibronectin and gelatin were added to this volume at a ratio of 0.05 mg fibronectin/mg particles. This mixture was shaken overnight (>10 hours) at 450 rpm and 4° C.

Todisperse aggregations formed during the shaking process, and sufficient polyethylene glycol (PEG; USP) was added to make the mixture 0.001% PEG. Unreacted reagents were removed by centrifugation at 1,000 rcf, followed by 3 washes with sterilized RO water, and subsequent filtration through a 100 kDa filter (EMD Millipore Amicon Ultra-4). The supernatants were combined, and unconjugated fibronectin was quantified with the Bradford protein assay (Thermo Scientific) using bovine serum albumin (BSA) as the standard. Fibronectin-conjugated particles were stored in PBS at 4° C. and used for cell seeding within one week.

Example 3: Microparticle Characterization

The shape, size, and surface topography of microparticles were analyzed with SEM at 1-10 kV and 150× to 250× magnification (Hitachi S-4700) and stereo microscopy (Hirox KH-8700). Particle size and shape were also visualized with bright field microscopy (Nikon Eclipse E400). The microparticle surface charge was measured in water and phosphate buffer saline (PBS; Fisher Scientific) with dynamic light scattering (DLS; Malvern NanoSeries Zetasizer ZS90). DLS measurements were performed at 25° C. in disposable capillary cells (Malvern) using the backscattering detection at 90°. The zeta potential was measured for 20 successive runs. Data was analyzed using means and standard deviations of three measurements.

Results

Figure 1:
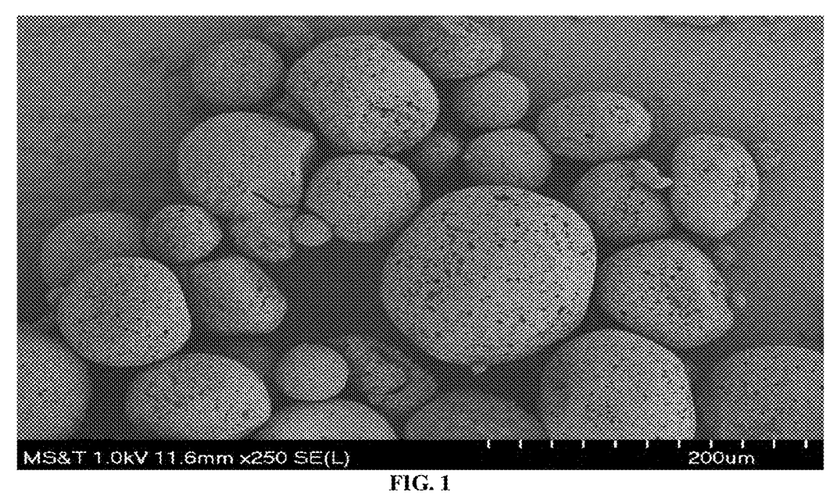
FIG. 1 depicts scanning electron microscope (SEM) images of PLGA microparticles of ~100 μm diameter.
Figure 2A:
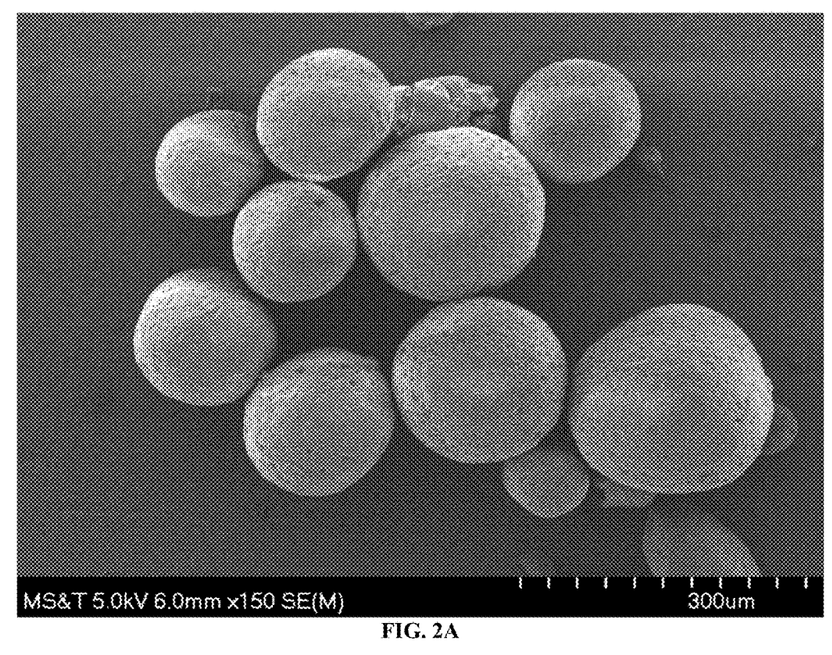
FIG. 2A depicts SEM images of PLGA microparticles.
Figure 2B:
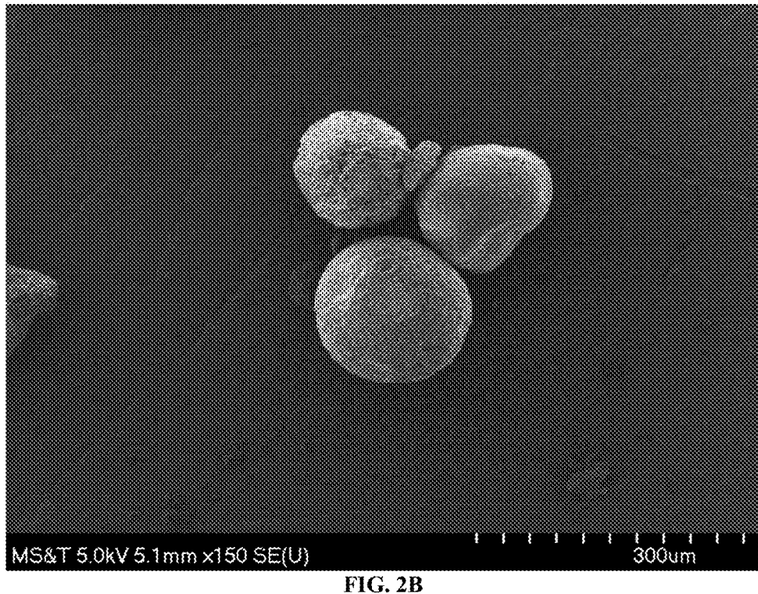
FIG. 2B depicts SEM images of PLGA-Gelatin (Gel) microparticles.
Figure 2C:
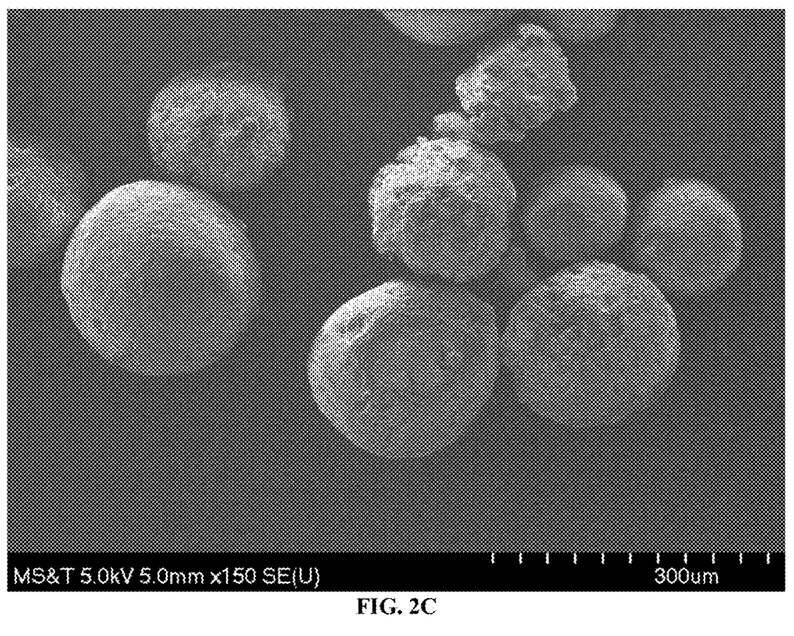
FIG. 2C depicts SEM images of PLGA-fibernectin (FN) microparticles.
Figure 2D:
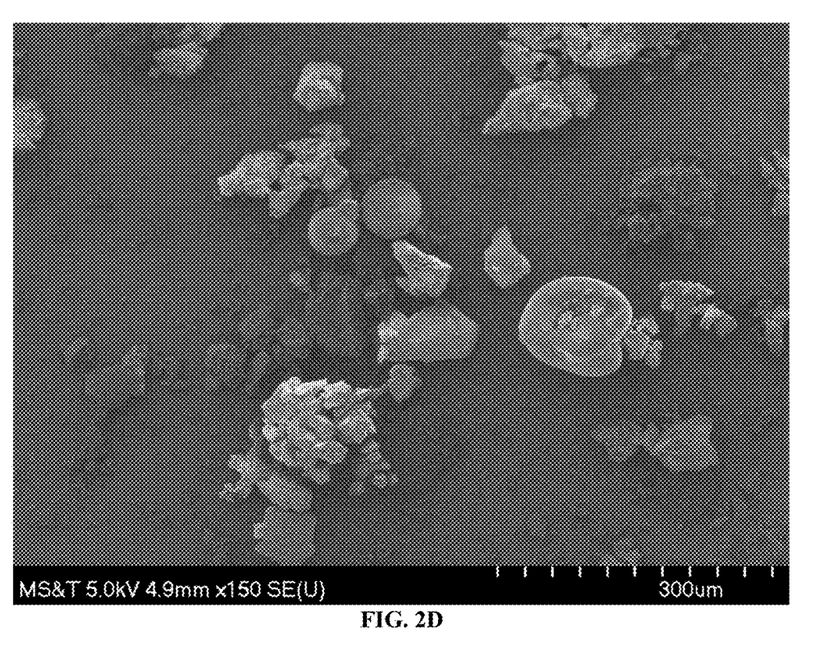
FIG. 2D depicts SEM images of PLGA-Gel-FN microparticles.
Figure 2E:
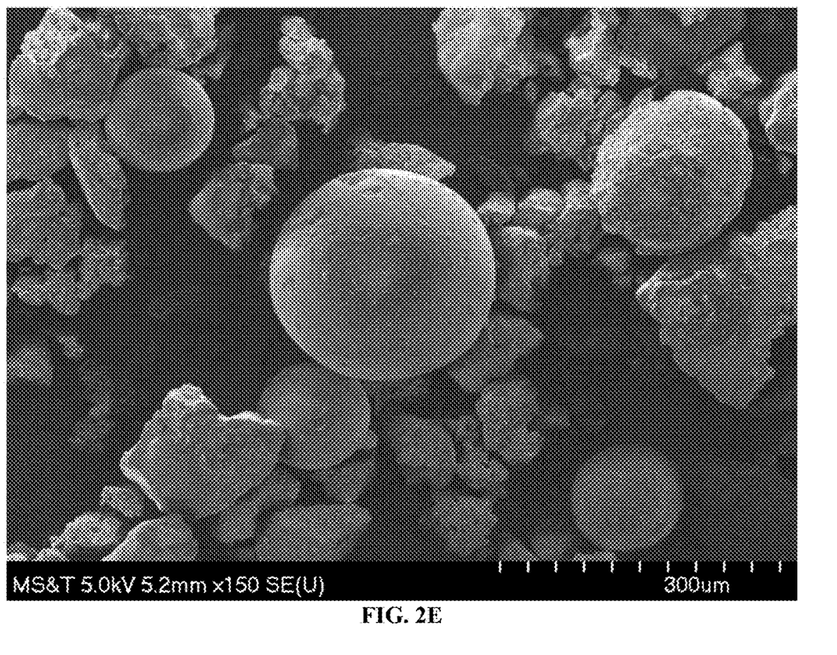
FIG. 2E depicts SEM images of PLGA-polyethyleneglycol (PEG)-Gel microparticles.
Figure 2F:
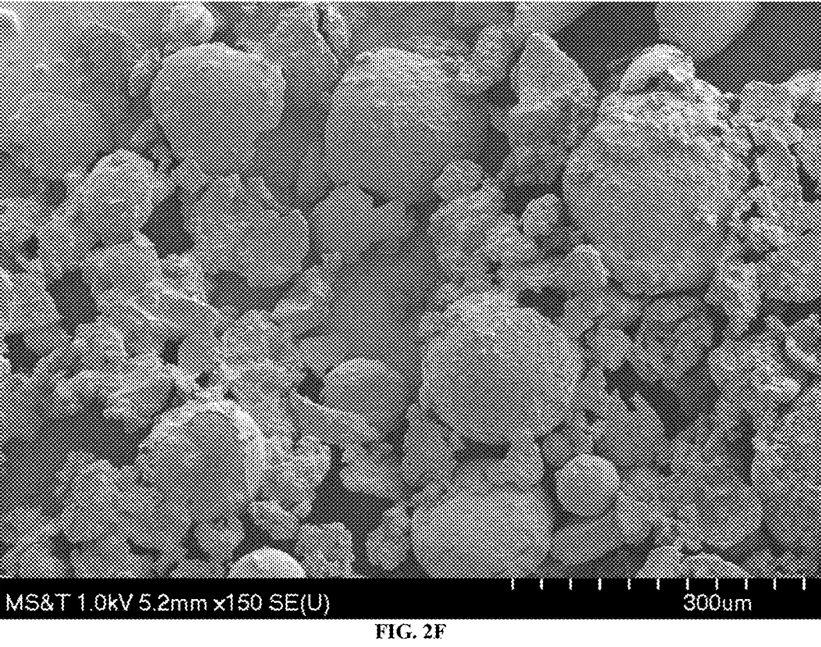
FIG. 2F depicts SEM images of PLGA-PEG-FN microparticles.
Figure 3:
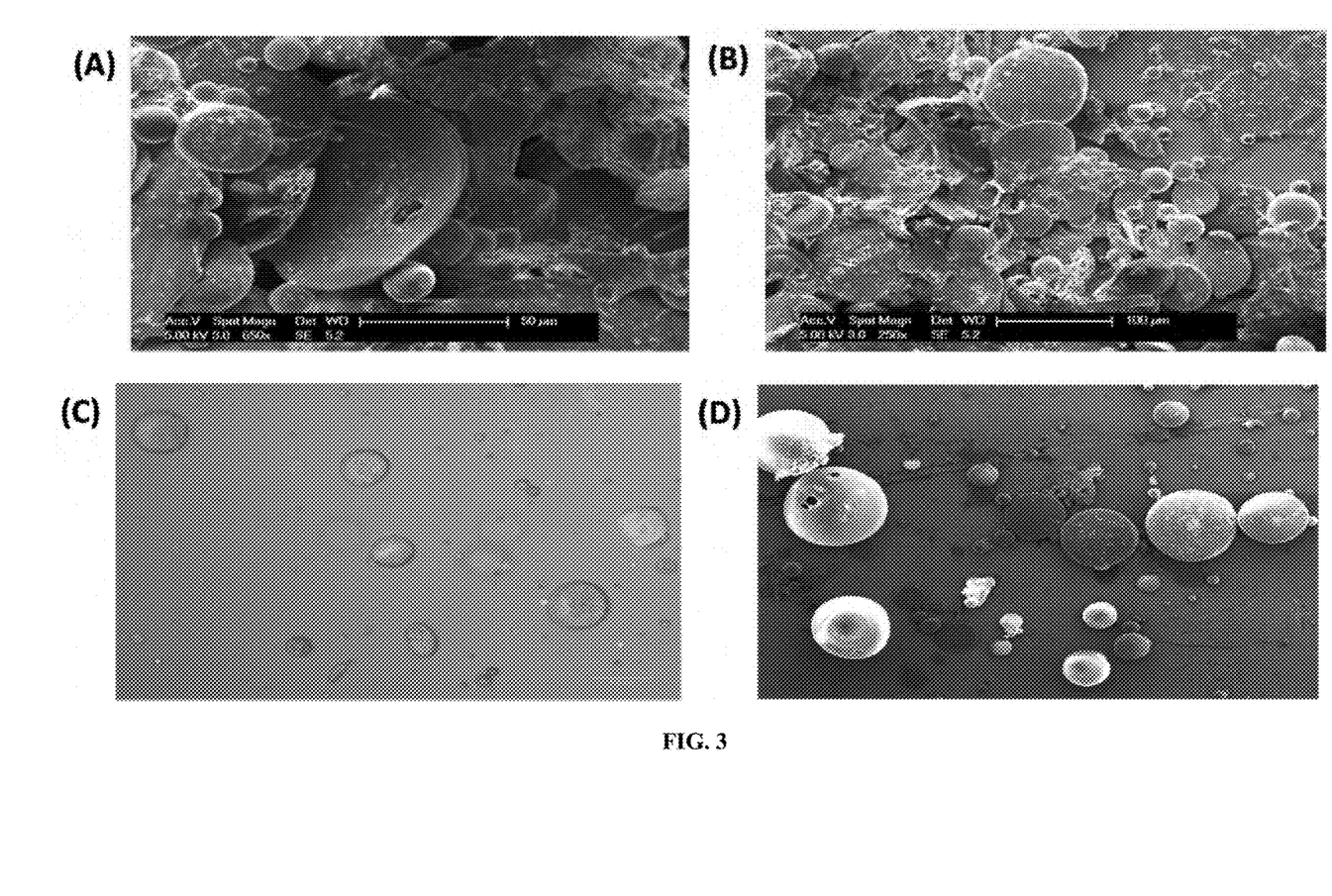
FIG. 3 depicts SEM, fluorescence microscopy, and Bright field microscopy of PLGA-gelatin disk microparticles.
Figure 4:
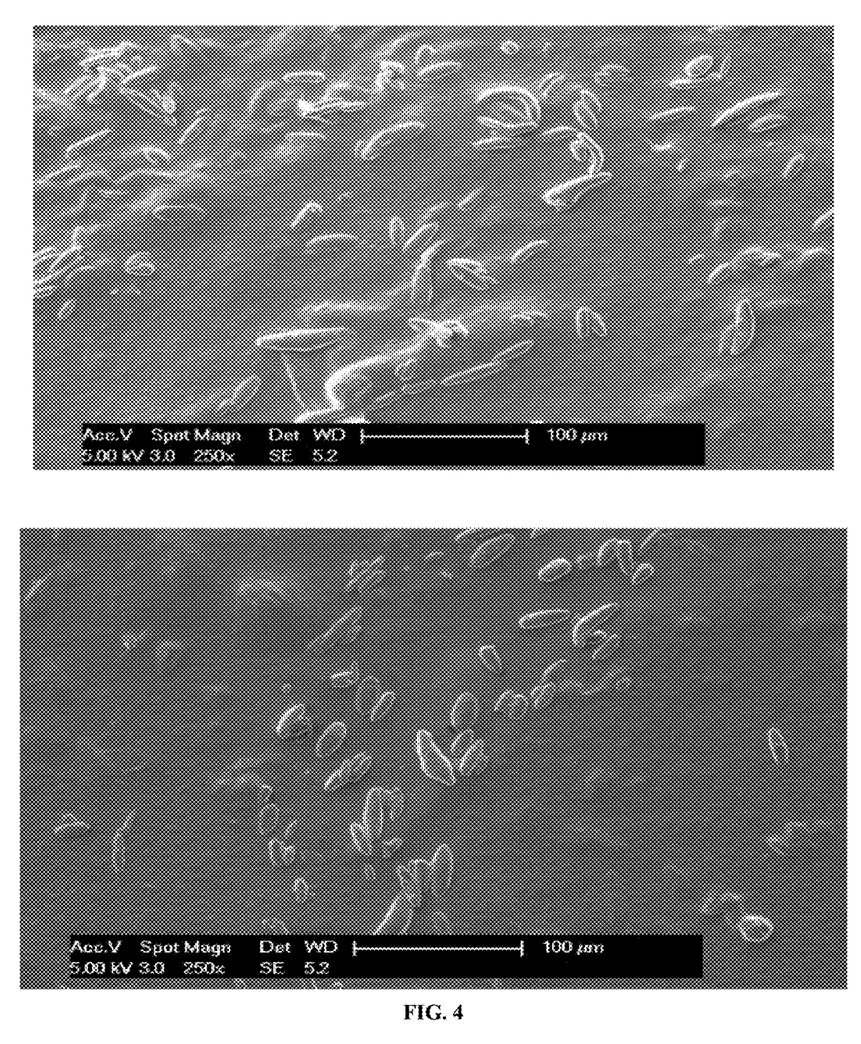
FIG. 4 depicts SEM images of rod shaped microparticles.

SEM images of particle formulations useable in cell seeding are shown in FIG. 1 (PLGA microspheres with average particle diameter 183±70 μm), and FIGS. 2A (PLGA), 2B (PLGA-Gelatin (Gel)), 2C (PLGA-fibernectin (FN)), 2D (PLGA-Gel-FN), 2E (PLGA-polyethyleneglycol (PEG)-Gel) and 2F (PLGA-PEG-FN). FIG. 3 depicts in panels (A) and (B) SEM images of PLGA-Gelatin disk shape microparticles of the following dimensions: 81±26 μm; width: ~2 surface area (S.A.): ~10,000 μm$^2$. Panel (C) of FIG. 3 depicts results of Fluorescence microscopy of FITC dye conjugated PLGA disks, and panel (C) depicts results of bright field microscopy of PLGA-gelatin disks microparticles. FIG. 4 depicts PLGA rod shaped microparticles of length of ~30 μm, width ~8±1.7 μm, and S.A. of ~570 μm$^2$.

Adding fibronectin increased particle stability and increased particle size significantly. Average particle diameter was determined using ZENPro imaging software which was package with the Zeiss Axis confocal microscope. Standard deviations were performed with at least n=50 particles. Number of particle per gram was determined using a known correlation (REF) based on polymer density and average particle diameter, as shown in Table 1.

TABLE 1

Average Particle Diameter and Particle Mass Density

| Particle Type | Average Particle Diameter | No. of Particles/g |
|---|---|---|
| PLGA | 183 ± 70.0 µm | 222,600 |
| PLGA-Gel | 214 ± 67.0 µm | 139,200 |
| PLGA-FN | 233 ± 37.8 µm | 107,850 |
| PLGA-PEG | 161 ± 30.1 µm | 326,900 |
| PLGA-PEG-Gel | 162 ± 43.3 µm | 320,900 |
| PLGA-PEG-FN | 180 ± 42.5 µm | 233,900 |

The conjugation efficiency of fibronectin binding to PLGA and PLGA-PEG particles was determined using the Bradford Protein Assay. Fibronectin was found to bind with 90% efficiency. Results are shown in Table 2. Free protein describes protein that did not bind to the microparticle.

TABLE 2

Fibronectin conjugation efficiency

| Particle | Mass Protein Initial | Mass of Free Protein | Mass Protein Conjugated | Conjugation Efficiency | Protein Density (µg Protein/cm² Particle) |
|---|---|---|---|---|---|
| | | Fibronectin Study | | | |
| PLGA | 116 µg | 7.02 ± 3.44 µg | 109 ± 3.44 µg | 94.0 ± 2.97% | 28.2 ± 0.890 |
| PLGA-PEG | 116 µg | 5.13 ± 1.03 µg | 111 ± 1.03 µg | 95.6 ± 0.888% | 22.2 ± 0.206 |

Figure 5:
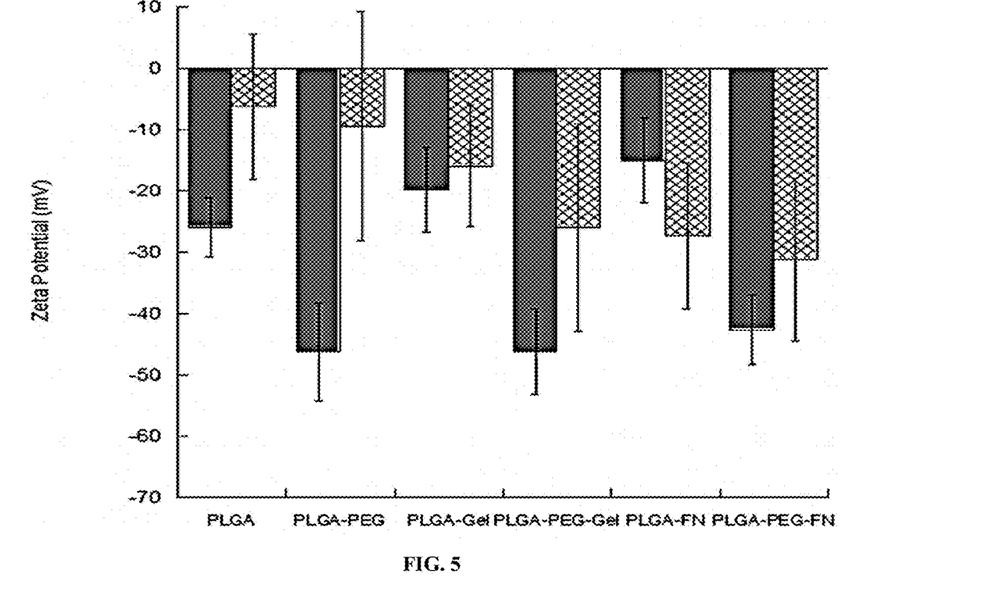
FIG. 5 is a graph of zeta potential of various particle types.

Fibronectin and gelatin were conjugated to the surface of both PLGA and PLGA-PEG particle types to improve the particle's association with fibroblast cells. The zeta potential of the microparticles was determined using a Nanoseries Zetasizer. Zeta potential was measured by diluting particles to a concentration of 3 mg/ml and measuring the electrophoretic mobility of the particles in RO water and phosphate buffered saline (PBS). Standard deviation was determined by n=3 trials for each microparticle. Results are shown in Table 3, below and FIG. 5. The zeta potential was found to be −25.9±4.8 mV in deionized water (DI $H_2O$) and −6.3±11.8 mV in PBS of pH 7.4.

TABLE 3

Zeta Potential of Particle Types

| Particle | ζ (mV) in $H_2O$ | ζ (mV) in PBS |
|---|---|---|
| PLGA | −25.9 ± 4.80 mV | −6.26 ± 11.8 mV |
| PLGA-Gel | −19.9 ± 8.02 mV | −16.0 ± 18.6 mV |
| PLGA-FN | −15.1 ± 6.9 mV | −27.4 ± 9.89 mV |
| PLGA-PEG | −46.3 ± 6.88 mV | −9.49 ± 16.9 mV |
| PLGA-PEG-Gel | −46.2 ± 6.94 mV | −26.0 ± 11.9 mV |
| PLGA-PEG-FN | −42.7 ± 5.64 mV | −31.1 ± 13.3 mV |

Example 3: Cell Growth of Microparticles In Vitro

Whether model cell line human umbilical vascular endothelial cells (HUVEC) attach to microparticles in suspension was investigated. HUVEC were cultured in Medium 200 containing low serum growth supplement (LSGS) and 1% penicillin/streptomycin at 37° C. and 5% $CO_2$. Cells were grown, and sub-cultured using the standard method. To this end, the appropriate ratio of cell to particle numbers was determined. The surface area ratios of cells to microparticles were calculated theoretically. A surface area ratio of 10 was reasonable. $1\times10^6$ HUVEC were seeded on $10^5$ number of each of disk, rod and spherical shaped microparticles in a bioreactor at 37° C. and 5% $CO_2$. After 24 h, a fluorescence microscope using DAPI nuclear stain imaged cell attachment. The number of live cells were quantified, and compared.

Figure 6:
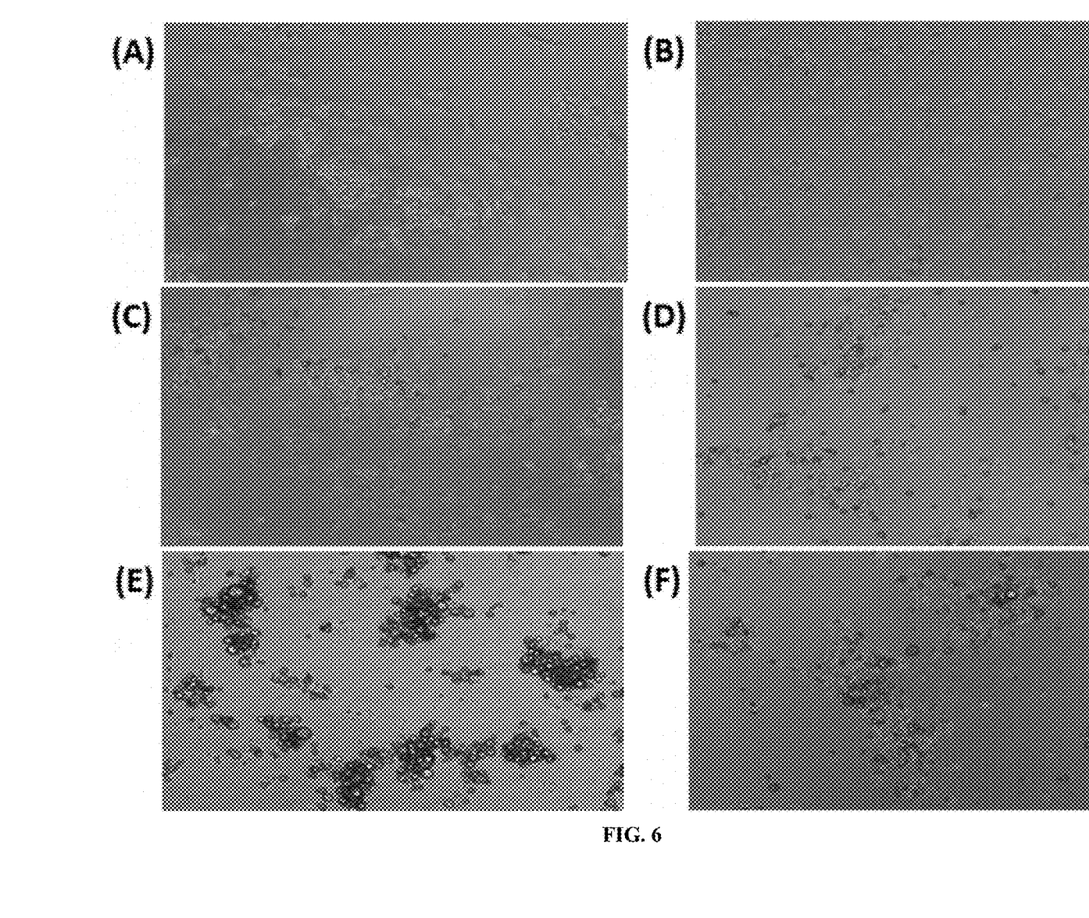
FIG. 6 depicts fluorescence microscope images of cell lines grown on various particle types.
Figure 7:
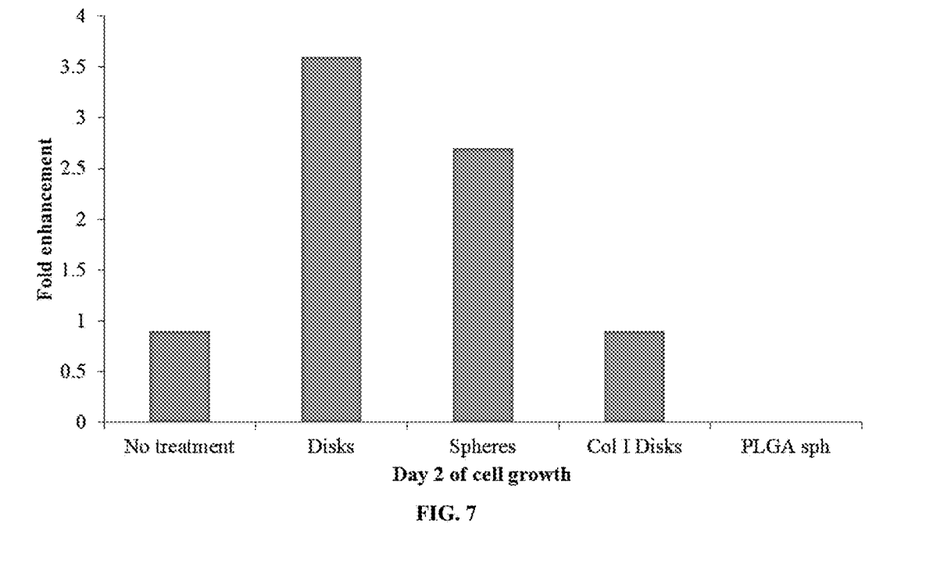
FIG. 7 is a graph of cell growth on various particle types.

FIG. 6 depicts fluorescence microscope images of a model cell line (HUVEC), grown on (a) a tissue-culture treated plate (control); (b) gelatin-coated tissue culture plate (control); (c) PLGA spheres; (d) PLGA disks; (e) gelatin-coated PLGA spheres; and (f) collagen-coated PLGA spheres. The blue fluorescence indicates cell nuclei. FIG. 7 is a graph of HUVEC growth on various particle shapes. Microparticles enhance the expansion of HUVEC. Disks show 1.4 fold more HUVEC growth than spheres. The attachment of cells to a microparticle surface is often seen as a basic characteristic. However, the microparticles geometry may subsequently influence and regulate the cell growth and survival.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A method for forming microparticles useful for cell seeding comprising:
   obtaining an organic solution comprising poly(D,L-lactide-co-glycolide) (PLGA);
   obtaining a first aqueous solution comprising polyvinyl alcohol (PVA);
   obtaining a second aqueous solution comprising PVA in a higher concentration than said first aqueous solution;
   co-injecting a stream of the organic solution and a carrier stream of the first aqueous solution into a flow focusing tube to form organic droplets within the carrier stream;
   introducing the carrier stream comprising the organic droplets into the second aqueous solution to form microparticles of the PLGA in the second aqueous solution;
   evaporating the organic solvent; and removing the PVA, wherein the ratio of the PLGA to the organic solvent is from 5% (w/v) to 15% (w/v).

2. A method for forming microparticles useful for cell seeding comprising:
obtaining an organic solution comprising poly(D,L-lactide-co-glycolide) (PLGA) and polyethylene glycol (PEG);
obtaining a first aqueous solution comprising polyvinyl alcohol (PVA);
obtaining a second aqueous solution comprising PVA in a higher concentration than said first aqueous solution;
co-injecting a stream of the organic solution and a carrier stream of the first aqueous solution into a flow focusing tube to form organic droplets within the carrier stream;
introducing the carrier stream comprising the organic droplets into the second aqueous solution to form microparticles of the PLGA in the second aqueous solution;
evaporating the organic solvent; and
removing the PVA, wherein the ratio of PLGA to PEG is greater than 70:1.

3. A method for forming microparticles useful for cell seeding comprising:
obtaining an organic solution comprising poly(D,L-lactide-co-glycolide) (PLGA);
obtaining a first aqueous solution comprising polyvinyl alcohol (PVA);
obtaining a second aqueous solution comprising PVA in a higher concentration than said first aqueous solution;
co-injecting a stream of the organic solution and a carrier stream of the first aqueous solution into a flow focusing tube to form organic droplets within the carrier stream;
introducing the carrier stream comprising the organic droplets into the second aqueous solution to form microparticles of the PLGA in the second aqueous solution;
evaporating the organic solvent; and
removing the PVA, wherein the ratio of the organic solution to the first aqueous solution is 1:1 to 1:10.

4. A method for forming microparticles useful for cell seeding comprising:
obtaining an organic solution comprising poly(D,L-lactide-co-glycolide) (PLGA);
obtaining a first aqueous solution comprising polyvinyl alcohol (PVA);
obtaining a second aqueous solution comprising PVA in a higher concentration than said first aqueous solution;
co-injecting a stream of the organic solution and a carrier stream of the first aqueous solution into a flow focusing tube to form organic droplets within the carrier stream;
introducing the carrier stream comprising the organic droplets into the second aqueous solution to form microparticles of the PLGA in the second aqueous solution;
evaporating the organic solvent;
removing the PVA, and after said removing step, the step of stretching the PLGA microparticles into microdisks and microrods.

5. The method of claim 1, wherein the organic solution further comprises polyethylene glycol (PEG).

6. The method of claim 5, wherein the ratio of PLGA to PEG is greater than 70:1.

7. The method of claim 1, wherein the concentration of PVA in the first aqueous solution is from 1% (w/v) to 10% (w/v).

8. The method of claim 1, wherein the concentration of PVA in the second aqueous solution is from 1% (w/v) to 10% (w/v).

9. The method of claim 1, wherein the ratio of the organic solution to the first aqueous solution is 1:1 to 1:10.

10. The method of claim 9, wherein the ratio of the organic solution to the first aqueous solution is 1:2 to 1:4.

11. The method of claim 9, wherein the ratio of the organic solution to the first aqueous solution to the second aqueous solution is from 1:1:5 to 1:5:25.

12. The method of claim 1, further comprising after said introducing step, stirring the second aqueous solution.

13. The method of claim 1, further comprising after said removing step, lyophilizing the PLGA microparticles.

14. The method of claim 1, further comprising after said removing step, the step of stretching the PLGA microparticles into microdisks and microrods.

15. A method of conjugating a cell binding protein to surfaces of poly(D,L-lactide-co-glycolide) (PLGA) microparticles comprising:
obtaining PLGA microparticles formed from the process of claim 1;
suspending the PLGA microparticles in an aqueous buffer solution at pH from 5.5 to 6.5;
activating carboxyl groups on the surfaces of the PLGA microparticles;
adding the protein to form a mixture of the microparticles and the protein at a pH above 7.0;
shaking the mixture to conjugate the protein to the surfaces of the PLGA microparticles; and
removing unreacted reagents.

16. The method of claim 15, wherein the ratio of the PLGA microparticles to the buffer solution is 1:1 to 25:1 (w/v).

17. The method of claim 15, wherein the protein is selected from the group consisting of fibronectin, gelatin, collagen, laminin, and peptides.

18. The method of claim 15, wherein the PLGA microparticles comprise PLGA-PEG microparticles.

19. The method of claim 15, wherein said removing step comprises centrifugation, filtration or combinations thereof.

20. The method of claim 2, wherein the ratio of the PLGA to the organic solvent is from 1% (w/v) to 25% (w/v).

21. The method of claim 20, wherein the ratio of the PLGA to the organic solvent is from 5% (w/v) to 15% (w/v).

22. The method of claim 2, wherein the concentration of PVA in the first aqueous solution is from 1% (w/v) to 10% (w/v).

23. The method of claim 2, wherein the ratio of the organic solution to the first aqueous solution is 1:1 to 1:10.

24. The method of claim 23, wherein the ratio of the organic solution to the first aqueous solution is 1:2 to 1:4.

25. The method of claim 23, wherein the ratio of the organic solution to the first aqueous solution to the second aqueous solution is from 1:1:5 to 1:5:25.

26. The method of claim 2, further comprising after said introducing step, stirring the second aqueous solution.

27. The method of claim 2, further comprising after said removing step, lyophilizing the PLGA microparticles.

28. The method of claim 2, further comprising after said removing step, the step of stretching the PLGA microparticles into microdisks and microrods.

29. A method of conjugating a cell binding protein to surfaces of poly(D,L-lactide-co-glycolide) (PLGA) microparticles comprising:
obtaining PLGA microparticles formed from the process of claim 2;

suspending the PLGA microparticles in an aqueous buffer solution at pH from 5.5 to 6.5;

activating carboxyl groups on the surfaces of the PLGA microparticles;

adding the protein to form a mixture of the microparticles and the protein at a pH above 7.0;

shaking the mixture to conjugate the protein to the surfaces of the PLGA microparticles; and removing unreacted reagents.

30. The method of claim 29, wherein the ratio of the PLGA microparticles to the buffer solution is 1:1 to 25:1 (w/v).

31. The method of claim 29, wherein the protein is selected from the group consisting of fibronectin, gelatin, collagen, laminin, and peptides.

32. The method of claim 29, wherein the PLGA microparticles comprise PLGA-PEG microparticles.

33. The method of claim 29, wherein said removing step comprises centrifugation, filtration or combinations thereof.

34. The method of claim 3, wherein the ratio of the PLGA to the organic solvent is from 1% (w/v) to 25% (w/v).

35. The method of claim 34, wherein the ratio of the PLGA to the organic solvent is from 5% (w/v) to 15% (w/v).

36. The method of claim 3, wherein the organic solution further comprises polyethylene glycol (PEG).

37. The method of claim 36, wherein the ratio of PLGA to PEG is greater than 70:1.

38. The method of claim 3, wherein the concentration of PVA in the first aqueous solution is from 1% (w/v) to 10% (w/v).

39. The method of claim 3, wherein the concentration of PVA in the second aqueous solution is from 1% (w/v) to 10% (w/v).

40. The method of claim 3, wherein the ratio of the organic solution to the first aqueous solution is 1:2 to 1:4.

41. The method of claim 3, wherein the ratio of the organic solution to the first aqueous solution to the second aqueous solution is from 1:1:5 to 1:5:25.

42. The method of claim 3, further comprising after said introducing step, stirring the second aqueous solution.

43. The method of claim 3, further comprising after said removing step, lyophilizing the PLGA microparticles.

44. The method of claim 3, further comprising after said removing step, the step of stretching the PLGA microparticles into microdisks and microrods.

45. A method of conjugating a cell binding protein to surfaces of poly(D,L-lactide-co-glycolide) (PLGA) microparticles comprising:

obtaining PLGA microparticles formed from the process of claim 3;

suspending the PLGA microparticles in an aqueous buffer solution at pH from 5.5 to 6.5;

activating carboxyl groups on the surfaces of the PLGA microparticles;

adding the protein to form a mixture of the microparticles and the protein at a pH above 7.0;

shaking the mixture to conjugate the protein to the surfaces of the PLGA microparticles; and removing unreacted reagents.

46. The method of claim 45, wherein the ratio of the PLGA microparticles to the buffer solution is 1:1 to 25:1 (w/v).

47. The method of claim 45, wherein the protein is selected from the group consisting of fibronectin, gelatin, collagen, laminin, and peptides.

48. The method of claim 45, wherein the PLGA microparticles comprise PLGA-PEG microparticles.

49. The method of claim 45, wherein said removing step comprises centrifugation, filtration or combinations thereof.

50. The method of claim 4, wherein the ratio of the PLGA to the organic solvent is from 1% (w/v) to 25% (w/v).

51. The method of claim 50, wherein the ratio of the PLGA to the organic solvent is from 5% (w/v) to 15% (w/v).

52. The method of claim 4, wherein the organic solution further comprises polyethylene glycol (PEG).

53. The method of claim 52, wherein the ratio of PLGA to PEG is greater than 70:1.

54. The method of claim 4, wherein the concentration of PVA in the first aqueous solution is from 1% (w/v) to 10% (w/v).

55. The method of claim 4, wherein the concentration of PVA in the second aqueous solution is from 1% (w/v) to 10% (w/v).

56. The method of claim 4, wherein the ratio of the organic solution to the first aqueous solution is 1:1 to 1:10.

57. The method of claim 56, wherein the ratio of the organic solution to the first aqueous solution is 1:2 to 1:4.

58. The method of claim 56, wherein the ratio of the organic solution to the first aqueous solution to the second aqueous solution is from 1:1:5 to 1:5:25.

59. The method of claim 4, further comprising after said introducing step, stirring the second aqueous solution.

60. The method of claim 4, further comprising after said removing step, lyophilizing the PLGA microparticles.

61. A method of conjugating a cell binding protein to surfaces of poly(D,L-lactide-co-glycolide) (PLGA) microparticles comprising:

obtaining PLGA microparticles formed from the process of claim 4;

suspending the PLGA microparticles in an aqueous buffer solution at pH from 5.5 to 6.5;

activating carboxyl groups on the surfaces of the PLGA microparticles;

adding the protein to form a mixture of the microparticles and the protein at a pH above 7.0;

shaking the mixture to conjugate the protein to the surfaces of the PLGA microparticles; and removing unreacted reagents.

62. The method of claim 61, wherein the ratio of the PLGA microparticles to the buffer solution is 1:1 to 25:1 (w/v).

63. The method of claim 61, wherein the protein is selected from the group consisting of fibronectin, gelatin, collagen, laminin, and peptides.

64. The method of claim 61, wherein the PLGA microparticles comprise PLGA-PEG microparticles.

65. The method of claim 61, wherein said removing step comprises centrifugation, filtration or combinations thereof.

* * * * *